United States Patent
Dunn

[19]

[11] Patent Number: 5,810,712
[45] Date of Patent: Sep. 22, 1998

[54] SURGICAL ENDOSCOPE SUPPORT AND PIVOT

[75] Inventor: Mary Elizabeth Dunn, North Oaks, Minn.

[73] Assignee: Ohio Medical Instrument Company, Inc., Cincinnati, Ohio

[21] Appl. No.: 702,329

[22] Filed: Sep. 27, 1996

[51] Int. Cl.$^6$ ........................................... A61B 1/04
[52] U.S. Cl. ........................................... 600/114; 604/174
[58] Field of Search ................................. 600/102, 114, 600/115, 117; 604/93, 117, 174, 177, 178, 180; 606/108, 130; 128/96.1, DIG. 26

[56] References Cited

U.S. PATENT DOCUMENTS

| | | | |
|---|---|---|---|
| 3,457,922 | 7/1969 | Ray | 606/130 |
| 4,633,865 | 1/1987 | Hengstberger et al. | 600/114 X |
| 5,184,601 | 2/1993 | Putman . | |
| 5,263,939 | 11/1993 | Wortrich | 604/174 |
| 5,279,575 | 1/1994 | Sugarbaker | 604/174 |
| 5,375,588 | 12/1994 | Yoon | 600/114 |
| 5,441,042 | 8/1995 | Putman . | |
| 5,556,385 | 9/1996 | Andersen | 604/174 |
| 5,658,272 | 8/1997 | Hasson | 606/108 X |

FOREIGN PATENT DOCUMENTS

| | | | |
|---|---|---|---|
| 6-54798 | 3/1994 | Japan | 600/114 |
| 90/13841 | 11/1990 | WIPO | 600/114 |

OTHER PUBLICATIONS

Brochure, OMI Surgical Products, a Division of Ohio Medical Instrument Company, Inc., *Mayfield®/ACCISS™*, 1996.

*Primary Examiner*—Beverly M. Flanagan
*Attorney, Agent, or Firm*—Gregory F. Cotterell

[57] ABSTRACT

A surgical endoscope support device for supporting a surgical endoscope at an end of a support arm over, and proximate to, a surgical site of a patient, the endoscope support device comprising a support and pivot body including a socket housing and a pivot ball, the socket housing having a centrally positioned inner bore in open communication between upper and lower surfaces, the inner bore having a spherical surface, and the pivot ball, positionable within the inner bore of the socket housing, in pivotable contact with the spherical surface of the inner bore, the pivot ball including a cylindrical bore through the center of the pivot ball, the cylindrical bore having a substantially uniform inner diameter along a long axis of the cylindrical bore, and an endoscope adapter having a substantially cylindrical outer wall and a substantially cylindrical central bore, the outer wall having an outer dimension substantially equivalent to the inner diameter of the cylindrical bore of the pivot ball for a sufficiently snug fit when the endoscope adapter is positioned within the cylindrical bore, the central bore of the adapter being adaptable for slidable telescoping engagement of the surgical endoscope through the central bore.

20 Claims, 3 Drawing Sheets

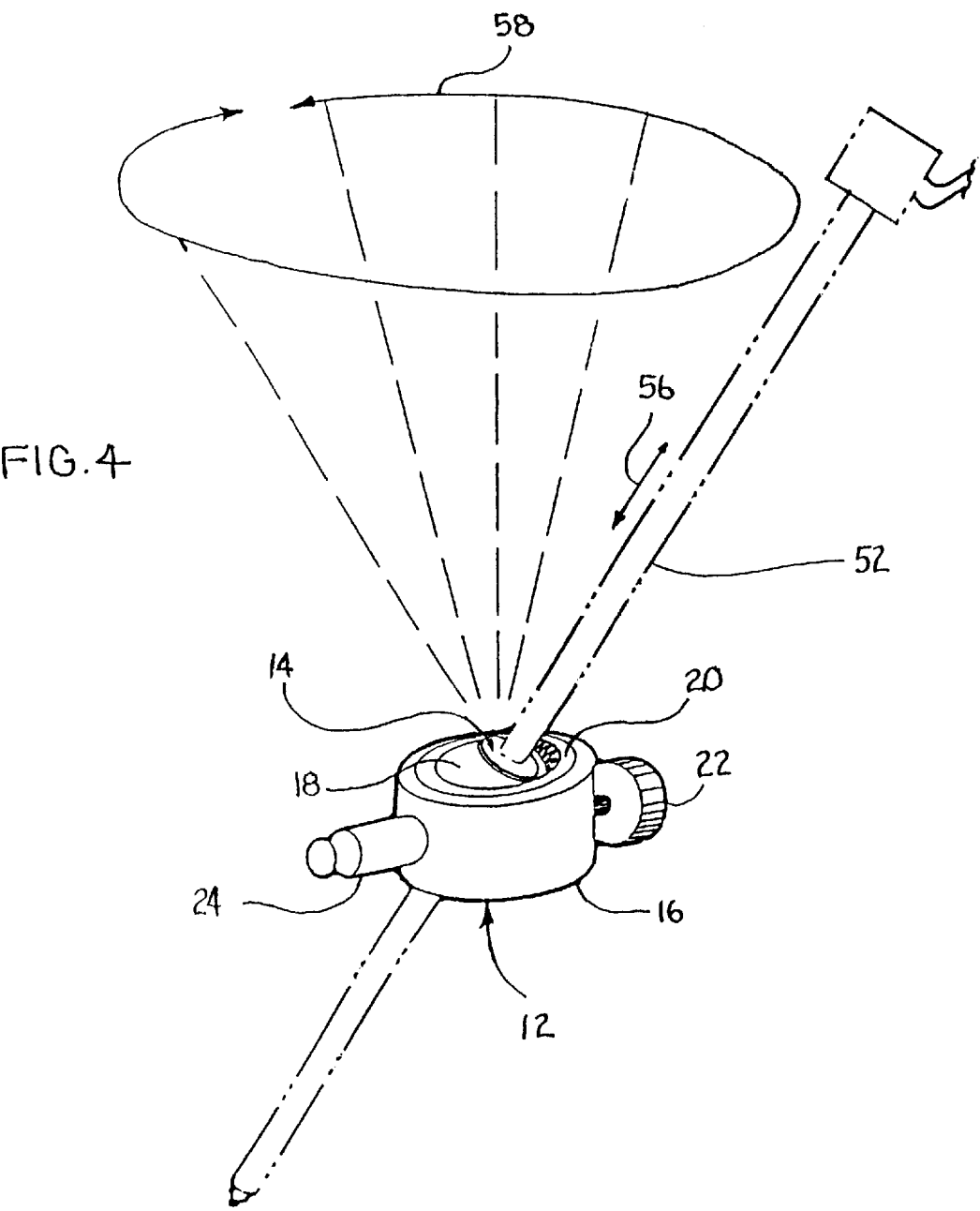

SURGICAL ENDOSCOPE SUPPORT AND PIVOT

FIELD OF THE INVENTION

This invention relates generally to positioning devices for supporting instruments and in particular to a support and pivot assembly for holding a surgical endoscope.

BACKGROUND OF THE INVENTION

The use of endoscopes to assist surgeons during surgical procedures has grown dramatically over the last several decades. For example, in surgical procedures involving the knee, the endoscope has become an indispensable tool for the surgeon in providing access within the patient through minimal incisions bringing in illumination, and through optics the surgeon may view the internal surgical field. One or more additional ports may also be available through which the surgeon may pass other surgical instruments, irrigation fluids, and/or vacuum for removing debris and irrigation fluids. Many endoscopes use fiber optics so that they may remain flexible and are useful for traversing long, tortuous channels such as the upper and lower gastrointestinal tracts.

Other endoscopes are rigid in nature and may or may not use internal optical fiber pathways. Rigid endoscopes are useful during procedures such as arthroscopy and laparoscopy because of the physical demands placed on the scopes during the procedures. The use of fiber optics has become increasingly popular because of its ability to be coupled with video imaging equipment. The surgeons and their assistants are able to all follow, as a group, the procedure on a video monitor versus the other alternative which is to look directly into the scope through an ocular lens system to directly view the procedure. This older method substantially precludes anyone besides the surgeon from directly viewing the surgical procedure.

As is often the case, once the endoscope has been positioned to view the operative procedure within the patient's body, the endoscope needs to be held stationary in that position for the period of time that the procedure is underway. Occasionally, the endoscope will be maneuvered in order to view the procedure from a different angle or to carry the operative procedure to a different area of the patient's body. Once the endoscope is maneuvered, it is then desirable to once again hold the endoscope stationary in that new position.

In the early days of operating with endoscopes, the surgeon was usually the person to insert the endoscope and also the one to hold the endoscope. This had the disadvantage of taking away at least one of the surgeon's hands from the operation. It was not too long before duties of holding the endoscope were passed along to assistants in the operating room who were called to assist in the case in order to hold the endoscope. The occasional repositioning would be undertaken by the surgeon after which the assistant would take over holding the scope. Either way, with the surgeon holding the scope or the assistant holding the endoscope, after a period of time the person becomes quite fatigued and their ability to hold the endoscope stationary markedly deteriorates. Untoward or unexpected movement of the endoscope at critical moments in the surgery could lead to very deleterious results, placing the patient in unnecessary danger.

Various mechanical means have been adapted for use in the operative field in order to stabilize endoscopes over long periods of time. One such device is known as a Greenfield support which essentially is a support using alternating cylinders and balls threaded over a cable attached to a mount at one end and a lever at the other end for placing the cable on tension. By levering a tension force through the cable, the alternating balls and cylinders are jammed together, stiffening the entire support arm. The distinct advantage in such a system is that the support, when loose is extremely flexible along its entire length, essentially being as floppy as the cable within. The support is positioned and then the cable is tensioned, the balls and cylinders stiffen into their prearranged positions and the support becomes stable in that position. Such a support is extremely versatile in providing for numerous positioning possibilities. The distinct disadvantage is that when the levering arm is released, the entire support becomes loose along its entire length from the instrument mounted at one end to the lever at the other end. Greenfield supports require the surgeon to carefully control the working head of the support prior to release of the tensioned cable. Attempts to reposition while tensioned also results in unexpected motions because no one can predict at which cylinder to ball interface the motion will occur. Motion may occur in a Greenfield support at a substantial distance unacceptably far from the operative site.

Alternative supports have been described using jointed retracting arms restrained to one to two degrees of freedom depending on the number of joints employed and the type of joint, but with an appropriate number of joints, pivoting about all three axes is attainable. The disadvantage of such systems is that motion about any given axis is carried out at distinctly different positions along the articulated support arm. Therefore, any motion along one of the three axes may necessarily have to be carried at a substantial distance unacceptably far from the operative site. For example, a motion in a joint that would cause translation of the endoscope may not be possible and possibly dangerous to the patient because of the endoscope's position within, and relative to, the patient's body and anatomical structures within the patient's body. Thus, even though these types of supports may allow for translation and rotation about all three axes, in reality these types of systems are severely limited because they do not take into account the physical restraints placed on the endoscope by virtue of its being positioned within the patient's body.

U.S. Pat. No. 5,441,042 issued to Putman on Aug. 15, 1995 is an example of just such a multi-articulated support arm. The endoscope instrument holder as contemplated by Putman has a clamp held distally on the arm with a knurled screw for clamping down on the endoscope body. There is no degree of freedom of motion at the clamp to endoscope junction. The first allowable motion is some distance away from and proximal to the clamp and as shown only provides motion in two of the three axes, one of those axes being translation along the long axis of the clamp and its associated rod. Consequently, simple rotation around the pivot proximal to the clamp will result in large motions of the endoscope through the arc of that pivot, having a radius equivalent to the length of the rod and the clamp. Such gross motions are usually not acceptable during a surgical procedure.

Surgeons relying on operating endoscopes need to be able to securely support the endoscope when positioned so that extraneous motion is eliminated but yet retain the ability to fine tune the positioning of the endoscope as the surgical procedure goes forward. There is a need for an endoscope support and pivot that will provide a surgeon the ability to stabilize the endoscope when needed and yet carry out fine translation and rotational motions, through all three planes, at the site of surgery.

SUMMARY OF THE INVENTION

The present invention discloses a surgical endoscope support device for supporting a surgical endoscope at an end of a support arm over, and proximate to, a surgical site of a patient comprising a socket housing and a pivot ball, the socket housing having substantially flattened upper and lower outer surfaces, an outer side surface between the upper and lower surfaces, and a centrally positioned inner bore communicating between the upper and lower surfaces, the inner bore having a spherical surface, the pivot ball, positionable within the inner bore of the socket housing, in pivotable contact with the spherical surface of the inner bore, the pivot ball including a cylindrical bore through the center of the pivot ball, the cylindrical bore having a substantially uniform inner diameter along a long axis of the cylindrical bore, the cylindrical bore adaptable for slidable telescoping engagement of the surgical endoscope through the cylindrical bore, and a universal type attachment for attaching the outer surface of the socket housing to any one of the many support arms available.

A preferred embodiment of the surgical endoscope support device comprises a support and pivot body and an endoscope adapter, the support and pivot body including a socket housing and a pivot ball, the socket housing having substantially flattened upper and lower outer surfaces, an outer side surface extending between the upper and lower surfaces, and a centrally positioned inner bore in open communication between the upper and lower surfaces, the inner bore having a spherical surface, and the pivot ball, positionable within the inner bore of the socket housing, in pivotable contact with the spherical surface of the inner bore, the pivot ball including a cylindrical bore through the center of the pivot ball, the cylindrical bore having a substantially uniform inner diameter along a long axis of the cylindrical bore, the endoscope adapter having a substantially cylindrical outer wall and a substantially cylindrical central bore, the outer wall having an outer dimension substantially equivalent to the inner diameter of the cylindrical bore of the pivot ball for a sufficiently snug fit when the endoscope adapter is positioned within the cylindrical bore, the central bore of the adapter being adaptable for slidable telescoping engagement of the surgical endoscope through the central bore and a universal type attachment for attaching the outer surface of the socket housing to any one of the many support arms.

The ball and socket design coupled with the central bore of the pivot ball, with or without the adapter, is useful to a surgeon using an endoscope to position the endoscope over the skin incision in the patient. The present invention provides for motion of the endoscope in all three planes from a single, localized point within the endoscope support and pivot. Therefore, the arc of rotation is no longer than that portion of the endoscope itself extending beyond the localized point. By placing the endoscope support and pivot proximate the skin of the patient, this radius, in essence, also becomes the smallest radius of motion possible. The surgeon may advance the endocsope into the patient or withdraw the endoscope in a slidable telescoping translation through the long axis of the central bore, and may translate the distal tip of the endoscope through an arc having a radius no longer than that length of endoscope extending from the endoscope support and pivot into the patient. Sideways translational movements of the endoscope at the skin surface of the patient are minimal, thus substantially limiting any sideways forces that the endoscope may exert on the tissues the endoscope traverses through and thus substantially diminishing the likelihood of injury to these tissues.

The endoscope support and pivot of the present invention may be constructed from any number of bio-compatible polymers, copolymers, metals and metal alloys suitable for use as surgical grade material capable of being cleaned and sterilizable in an autoclave or gas sterilizer. To facilitate cleaning, the invention anticipates the addition of a threaded retaining ring for use within the upper surface that, when removed, facilitates removal of the pivot ball from the inner bore of the socket housing.

The endoscope adapter is intended to have a snug fit within the central bore so as to not come out while using the endoscope. To facilitate a snug friction fit, the present invention anticipates the use of ribs raised in the outer surface of the endoscope adapter. These ribs are particular beneficial when the endoscope adapter is constructed with polymeric compounds that are deformable and are crushed when the endoscope adapter is pushed into the central bore.

The slidable telescoping fit between the endoscope adapter and endoscope should also maintain a gentle friction fit to eliminate inadvertent sliding of the endoscope when not pushing or pulling the endoscope. The present invention anticipates placing a slight taper at the lower end of the endoscope adapter bore narrowing the inner diameter. This is especially useful when using polymeric compounds that are deformable, yet retain some resiliency. Coupling the taper with selection of those polymers with greater surface lubrisity provides for a reasonably stable support of the endoscope, without movement through the endoscope adapter bore, unless under gentle urging by the surgeon.

An additional advantage of the present invention is use of a snub screw to increase control over the pivot ball. The pivot ball and socket may be constructed to tolerances that will provide sufficient friction between the parts to prevent motion unless urged to do so by the surgeon. Addition of a snub screw provides increased reliability in preventing unwanted and potentially dangerous movement of the endoscope.

Other objects of the present invention and many of the attendant advantages of the present invention will be readily appreciated as the same become better understood by reference to the following detailed description when considered in connection with the accompanying drawings.

BRIEF DESCRIPTION OF THE DRAWINGS

FIG. 4 is a perspective view of the present invention depicted in FIG. 1 shown set up with an endoscope, shown in phantom;

DETAILED DESCRIPTION OF THE INVENTION

Figure 1:
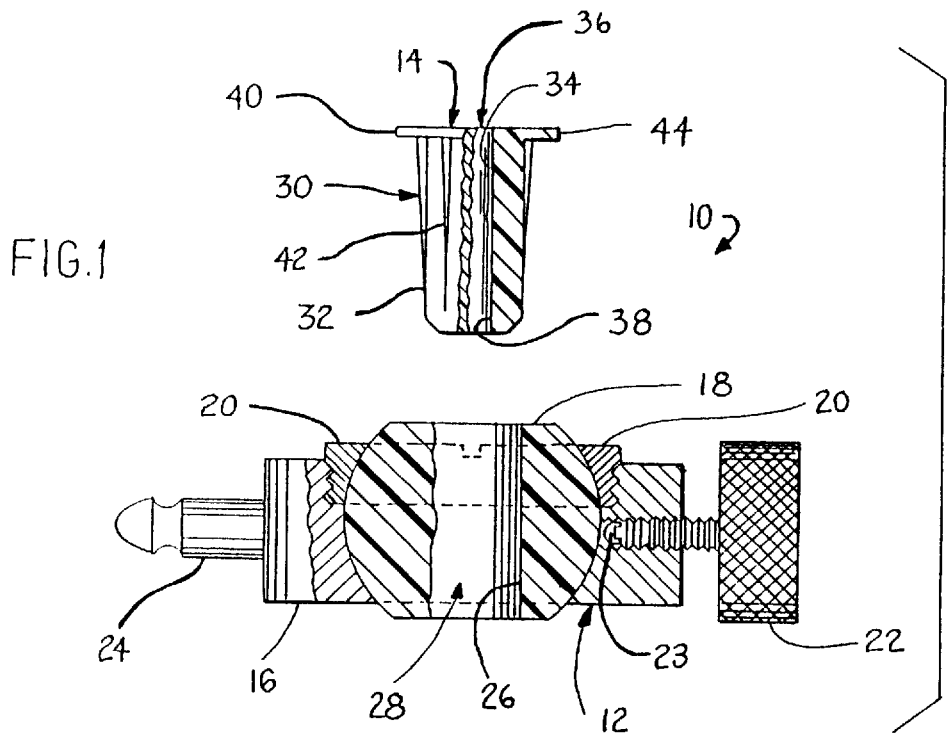
FIG. 1 is a partially cross sectioned, partially exploded, side elevational view of an embodiment of the present invention.
Figure 2:
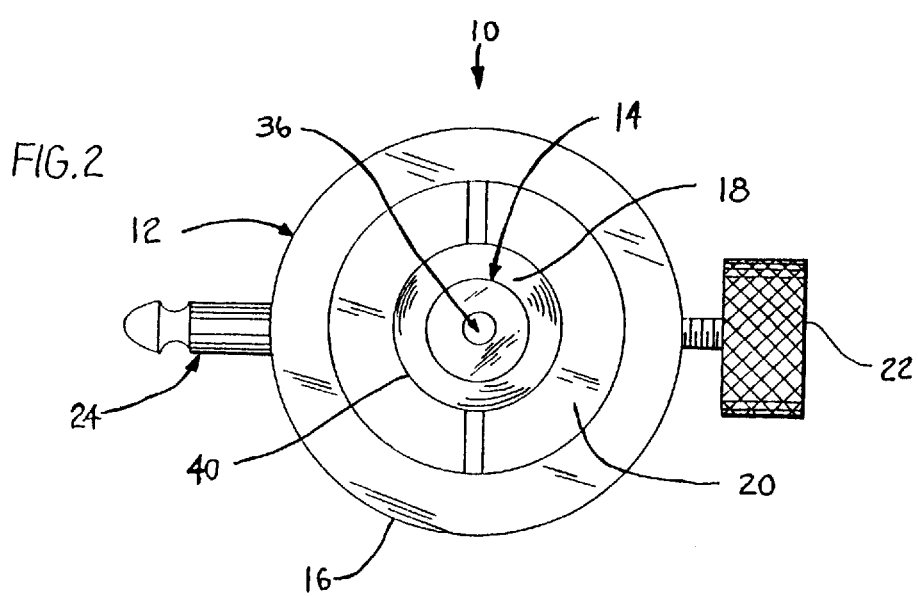
FIG. 2 is a top plan view of the embodiment of the present invention depicted in FIG. 1.

Referring to the Figures, wherein like numbers refer to like components, there is depicted in FIGS. 1 and 2 an embodiment of the present invention disclosed as an endoscope support and pivot head 10 including a pivot body 12 and an endoscope adapter 14. Pivot body 12 comprises a socket housing 16, a pivot ball 18 adapted to fit within socket housing 16, a pivot ball retaining ring 20, a pivot ball snub screw 22, and an adaptable support mount 24. Pivot ball 18 includes a central cylinder wall 26 defining a central bore 28.

Endoscope adapter 14 includes an adapter cylinder 30 having an outer cylinder wall 32 and an inner cylinder wall 34 which defines an adapter bore 36. Endoscope adapter 14 also includes an adapter taper 38 at the lower end of adapter bore 36, a stop flange 40, multiple fitting ribs 42 on outer cylinder wall 32 and a flange tab 44.

Pivot body 12 is comprised of a ball and socket joint mechanism wherein pivot ball 18 is free to articulate within socket housing 16. The present invention anticipates that these two components may be constructed out of any bio-compatible material that is suitable for use in surgical instruments and capable of undergoing sterilization in either an autoclave or through gas sterilization. There are a number of available materials such as stainless steel and other metal alloys as well as polymer and copolymer compounds including such polymers as polyvinyl chloride, polyethylene, and related plastics.

Strict adherence to surgical technique and sterilization necessitates that surgical instruments be thoroughly cleaned and sterilized. To facilitate removal of the pivot ball, ball retaining ring 20 has been incorporated into the design of socket housing 16 to provide ease of removal of pivot ball 18 from socket housing 16. Ball retaining ring 20 is threaded at its outer perimeter and has a spherical inner surface that matches, and is continuous with, the inner spherical surface of socket housing 16 when ball retaining ring 20 is threaded into place. Ball retaining ring 20 provides users of the present invention the ease of completely dismantling all the component parts for easy cleaning and sterilization as well as direct visualization of all of the component parts to ensure that all the parts are in proper working order and are thoroughly cleaned.

The present invention anticipates that pivot ball 18 is adaptable to receive an endoscope instrument through its central bore 28 in a relatively snug yet slidable telescoping arrangement. Since endoscopes come in various different outer diameters, pivot ball 18 may be manufactured so as to provide the user a selection of pivot balls, each having a different center bore inner diameter. Use of ball retaining ring 20 provides for easy removal of one pivot ball and replacement with another if the surgeon changes endoscopes having different outer diameters during a procedure.

Recognizing the versatility of the present invention, it is preferred that pivot ball 18 and socket housing 16 be manufactured as standard, single sized components. Endoscope adapter 14 may be used then as an alternative interface between an endoscope and adapter bore 36, with the inner diameter of central bore 28 and the outer diameter of outer cylinder wall 32 standardized and complementary to each other so as to fit snugly without unintended motion between the two components.

This has an advantage in that endoscope adapter 14, overall, is a smaller component than pivot ball 18. A number of different sizes of endoscope adapter 14, with varying diameters for adapter bore 36, are anticipated for the present invention and useful for supporting all endoscopes. The size range for the diameters of adapter bore 36 is as broad, and numerous, as are the number of endoscopes available now and in the future. Manufacturing costs are substantially less when using an insert such as endoscope adapter 14, because of its smaller size and having a standardized outer cylinder wall 32.

Endoscope adapter 14 may be manufactured from a number of different materials much like pivot body 12, and endoscope adapter 14 may also be disposable. The present invention anticipates that a set of multiple sizes of endoscope adapter 14 may be provided with each support and pivot head 10, each having a different internal diameter for adapter bore 36. The present invention also anticipates that multiple sizes of endoscope adapter 14 may be provided separately further diminishing costs. A surgical facility need only obtain one standard ball and socket that is re-sterilizable and reusable and purchase disposable sets of the smaller adapter.

Socket housing 16 and pivot ball 18 may be manufactured to provide sufficient friction between the mating surfaces of socket housing 16 and pivot ball 18 so as to provide adequate support for a mounted endoscope preventing independent motion of pivot ball 18 relative to socket housing 16. Such manufacturing, however, demands close tolerances and use of materials that will not easily break down over time when manufactured at such close tolerances. A useful addition is pivot ball snub screw 22 which provides the surgeon the capability of controlling the amount of friction, and thus the stability, of pivot ball 18 relative to socket housing 16. Additionally, a resilient polymeric or rubber snub screw tip 23 may be used in association with snub screw 22 at its contact with the surface of pivot ball 18 to diminish the likelihood of wear on the outer surface of pivot ball 18 in contact with snub screw 22.

Figure 3:
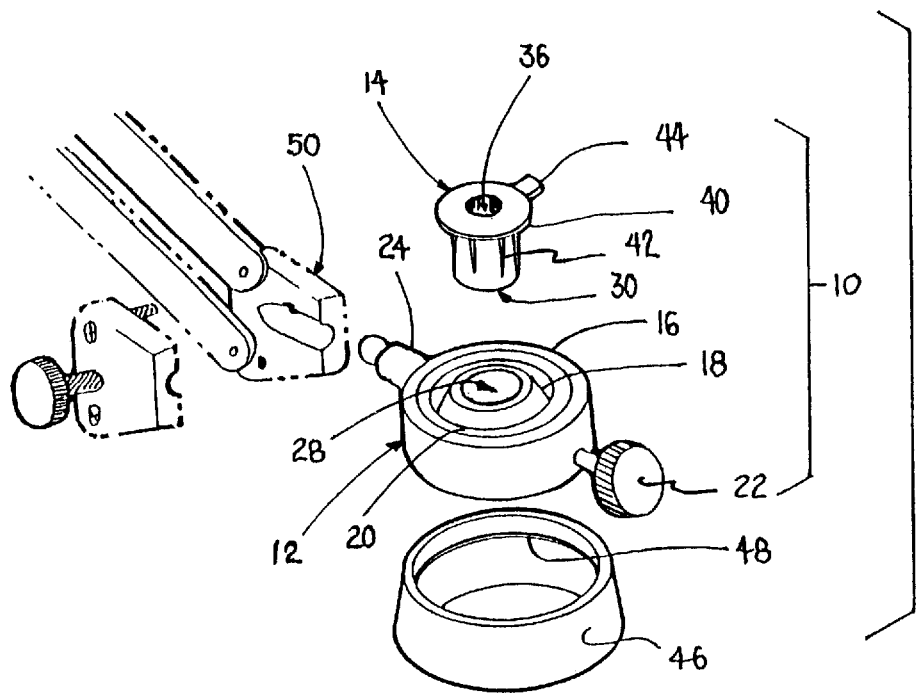
FIG. 3 is a perspective, partially exploded, view of the present invention depicted in FIG. 1 shown in relation to a typical support arm, shown in phantom.
Figure 5:
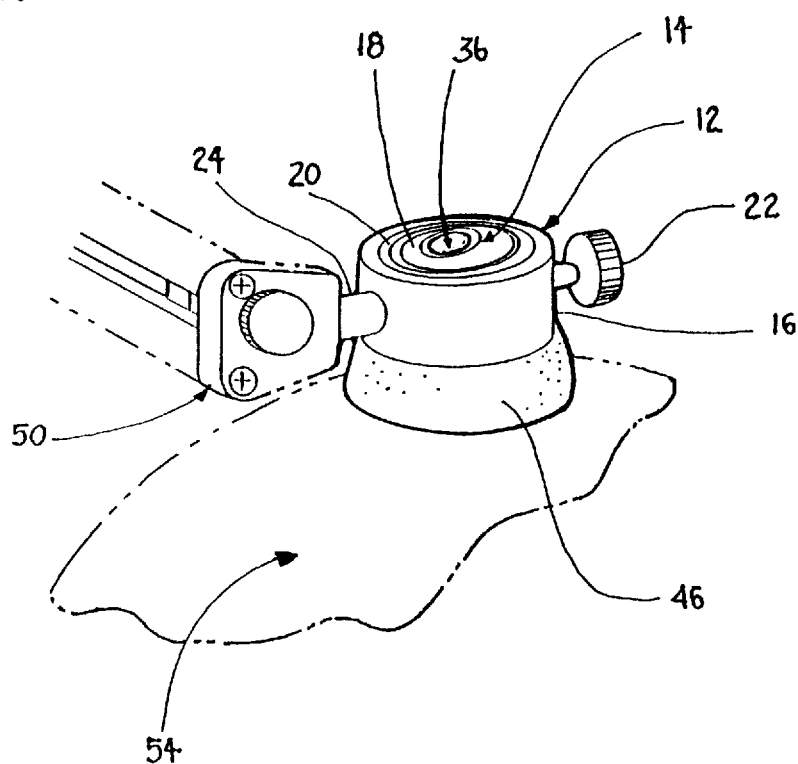
FIG. 5 is a perspective view of the present invention depicted in FIG. 3 shown set up in a typical support arm and positioned adjacent a portion of a patient, both shown in phantom.

Endoscope adapter 14 anticipates the use of several other optional features. One feature is multiple fitting ribs 42 on outer cylinder wall 32. Multiple fitting ribs 42 are useful for providing a substantially snug fit between endoscope adapter 14 and central cylinder wall 26 of pivot ball 18 when endoscope adapter 14 is pushed into central bore 28. As shown in FIGS. 1 and 3, ribs 42 are substantially parallel to the long axis of endoscope adapter 14. The present invention anticipates that ribs 42 may take on a number of different orientations, not shown, most notably as ribs circumferentially placed about the outer cylinder wall 32 transverse to the long axis of endoscope adapter 14.

Other optional additions to endoscope adapter 14 are flange 40 and flange tab 44. Flange 40 is useful as a stop when endoscope adapter 14 is pressed into central bore 28 of pivot ball 18. Flange tab 44 is useful for providing a grasping tab to facilitate removal of endoscope adapter 14. Flange tab 44 may be grasped by the surgeon or an assistant and also by using a surgical instrument such as a hemostat or clamp.

Endoscope adapter 14 also anticipates the use of adapter taper 38 to improve the fit between an endoscope and inner cylinder wall 34 of endoscope adapter 14. The adapter taper 38 is particularly useful when endoscope adapter 14 is manufactured out of a polymeric compound. The deformability of polymers, coupled with the general characteristics of resilience, enables adapter taper 38 to snugly fit against the surface of an endoscope. This snug fit, coupled with such factors as surface lubrisity of the polymers used, provides adequate support to the endoscope while still enabling slidable, telescoping movement of the endoscope relative to endoscope adapter 14 with gentle urging from the surgeon.

Turning to FIG. 3, there is also shown a skirt 46 with an inner rim ridge 48 for abutting against the lower edge of pivot body 12 when skirt 46 is placed on pivot body 12 as shown in FIG. 4. Skirt 46 is manufactured from polymers and preferably is a closed cell foam, but may be open cell or solid. Skirt 46 may also be used to further dampen unwanted vibrations in the entire system by acting as a vibration dampener when attached to pivot body 12 and then put in contact with the surface of the patient. This is particularly beneficial in neurosurgical applications where the risk of injury to the soft brain structures is markedly greater. The fine work and small space within which a neuroendoscope is placed also benefits from the vibration dampening effects of skirt 46.

Additionally, there is shown a support arm 50 adapted for receiving adaptable support mount 24. The type or structure of support arm 50 is of no particular importance to the present invention. The present invention is useful with all types and makes of support arms, such as Greenfield support arms or other articulated arms such as support arm 50. The type of support arm is immaterial because once the endoscope support and pivot of the present invention is put in place over the surgical field, the support arm is locked into its position and does not need to be moved again for the remainder of the surgical procedure. Therefore, support arm 50 may be of any type and adaptable support mount 24 may be changed to correspond to the mating portion of the support arm chosen.

In operation, and referring to FIGS. 1 through 5, the entire endoscope support and pivot head 10 is sterilized and then assembled by placing pivot ball 18 into socket housing 16 and screwing ball retaining ring 20 into place. In the preferred embodiment, an appropriate endoscope adapter 14 is chosen so as to match the outer diameter of the endoscope, such as an endocsope 52, that the surgeon will use. Endoscope adapter 14 is then pushed into central bore 28 of pivot ball 18 abutting flange 40 against pivot ball 18. An alternative arrangement of the present invention is to manufacture pivot ball 18 in a range of central bore 28 diameters. Then depending on the endoscope to be used, the pivot ball having the corresponding central bore 28 diameter is chosen and the endoscope is placed directly through central bore 28.

Endoscope support and pivot head 10 and a support arm, such as support arm 50, are then brought into the sterile surgical field. Endoscope support and pivot head 10 is mounted to the support arm at adaptable support mount 24 and pivot body 12 is positioned over the surgical site and incision in the patient. Skirt 46 may or may not be needed, but is shown in position in FIG. 4. Skirt 46 is mountable onto the lower portion of socket body 12 and useful as a barrier around the surgical incision site such as the trephine in a patient's skull surface 54.

Endoscope 52 is now positionable within central bore 36 of endoscope adapter 14 and is in slidable telescoping relation to central bore 36. Endoscope 52 is controllable by the operating surgeon in all three planes as shown by bidirectional arrow 56 in the z axis by slidable telescoping movement of the endoscope through adapter bore 36 along the long axis of endoscope adapter 14 and bidirectional arrow 58 for the x and y axes as provided by the articulation of pivot ball 18 in socket housing 16.

It is anticipated that the present invention is useful for all rigid endoscopes for all surgical procedures involving those rigid endoscopes in different anatomical locations. One such example is the use of a neuroendoscope within endoscope support and pivot 10 positioned over a trephine through a patient's skull to provide viewing and surgical access within a patient's brain. The endoscope may be slowly and methodically advanced through endoscope adapter 14 along the direction of bi-directional arrow 56. The pivoting relationship of pivot ball 18 to socket housing 16 allows the surgeon to impose pivoting directions in the x and y planes as is shown by bidirectional arrow 58. In this way, the surgeon is able to approach, reposition, back off and approach again to different anatomical structures within a patient's brain minimizing motion of the endoscope by localizing the pivot point to a single point within endoscope support and pivot 10 immediately adjacent to and just over the incision.

This endoscope motion control is a substantial improvement over the prior art. Use of a Greenfield or an articulating arm imposes translation motions that substantially exceed the total width of the trephine hole because motion may be imparted in these supports at articulation joints considerably distant from the surgical incision. Additionally, and particularly in neurosurgery, the soft structure of the brain is easily damaged by unacceptably extensive lateral or translational motions. With the present invention, lateral and translational motions are limited to an arc equal to just that length of the endoscope extending beyond the point of rotation of pivot ball 16. This is effectively a substantially smaller arc and radius when compared to the prior art where the radius of the arc includes not only the length of the endoscope, but also that portion of the articulating arm proximal to the endoscope involved in carrying out the motion.

The foregoing is considered as illustrative only of the principles of the invention, and since numerous modifications and changes will regularly occur to those skilled in the art, it is not desired to limit the invention to the exact construction and operation shown and described herein and accordingly, all suitable modifications and equivalents may be resorted to falling within the scope of the present invention.

I claim:

1. A surgical endoscope support device for supporting a surgical endoscope at an end of an external support arm over, and proximate to, a surgical site of a patient, the endoscope support device comprising:

a socket housing having substantially flattened upper and lower outer surfaces, an outer side surface between the upper and lower surfaces, and a centrally positioned inner bore communicating between the upper and lower surfaces, the inner bore having a spherical surface;

a pivot having substantially flattened upper and lower surfaces positionable within the inner bore of the socket housing, in pivotable contact with the spherical surface of the inner bore, such that the pivot lower surface extends beyond the socket housing lower surface, the pivot including a cylindrical bore through the center of the pivot, the cylindrical bore having a substantially uniform inner diameter along a long axis of the cylindrical bore, the cylindrical bore adaptable for slidable telescoping engagement of the surgical endoscope through the cylindrical bore; and means for attaching the outer surface of the socket housing to the external support arm.

2. The endoscope support device of claim 1 in which the socket housing includes a cylindrical counter bore in the upper surface centered around the open communication between the inner bore and the upper surface, the counter bore having a threaded wall, and further comprising a pivot retaining ring having an outer threaded surface complimentary to the threaded wall of the counter bore and a spherical inner surface such that when the pivot retaining ring is threaded into the counter bore, the spherical inner surface is continuous with the spherical surface of the inner bore of the socket housing.

3. The endoscope support device of claim 1 in which the socket housing includes a cylindrical side bore extending from the outer side to the inner bore along an axis directed towards the geometric center of the spherical surface of the inner bore, the side bore in open communication with the inner bore and the outer side, the side bore having a threaded wall, and further comprising a snub screw having complimentary thread to the threaded wall of the side bore such that an end of the screw, when threaded into the side bore, may abut the pivot.

4. The endoscope support device of claim 1 in which the socket housing and pivot are constructed with bio-compatible, sterilizable surgical grade metal.

5. The endoscope support device of claim 1 in which the socket housing and pivot are constructed with bio-compatible, sterilizable surgical grade polymer.

6. The endoscope support device of claim 1 in which the socket housing is constructed with bio-compatible, sterilizable surgical grade metal and the pivot is constructed with bio-compatible, sterilizable surgical grade polymer.

7. The endoscope support device of claim 1 further comprising a skirt positionable at the lower surface of the socket housing extending between the lower surface and the patient.

8. The endoscope support device of claim 7 in which the skirt is constructed with a resilient polymer.

9. A surgical endoscope support device for supporting a surgical endoscope at an end of an external support arm over, and proximate to, a surgical site of a patient, the endoscope support device comprising:

a support and pivot body including a socket housing and a pivot, the socket housing having substantially flattened upper and lower outer surfaces, an outer side surface extending between the upper and lower surfaces, and a centrally positioned inner bore in open communication between the upper and lower surfaces, the inner bore having a spherical surface, and the pivot having substantially flattened upper and lower surfaces positionable within the inner bore of the socket housing, in pivotable contact with the spherical surface of the inner bore, such that the pivot lower surface extends beyond the socket housing lower surface, the pivot including a cylindrical bore through the center of the pivot, the cylindrical bore having a substantially uniform inner diameter along a long axis of the cylindrical bore;

an endoscope adapter having a substantially cylindrical outer wall and a substantially cylindrical central bore, the outer wall having an outer dimension substantially equivalent to the inner diameter of the cylindrical bore of the pivot ball for a sufficiently snug fit when the endoscope adapter is positioned within the cylindrical bore, the central bore of the adapter being adaptable for slidable telescoping engagement of the surgical endoscope through the central bore; and means for attaching the outer surface of the socket housing to the external support arm.

10. The endoscope support device of claim 9 in which the socket housing includes a cylindrical counter bore in the upper surface centered around the open communication between the inner bore and the upper surface, the counter bore having a threaded wall, and further comprising a pivot retaining ring having an outer threaded surface complimentary to the threaded wall of the counter bore and an a spherical inner surface such that when the pivot retaining ring is threaded into the counter bore, the spherical inner surface is continuous with the spherical surface of the inner bore of the socket housing.

11. The endoscope support device of claim 9 in which the socket housing includes a cylindrical side bore extending from the outer side to the inner bore along an axis directed towards the geometric center of the spherical surface of the inner bore, the side bore in open communication with the inner bore and the outer side, the side bore having a threaded wall, and further comprising a snub screw having complimentary thread to the threaded wall of the side bore such that an end of the screw, when threaded into the side bore, may abut the pivot.

12. The endoscope support device of claim 9 in which the socket housing and pivot are constructed with bio-compatible, sterilizable surgical grade metal.

13. The endoscope support device of claim 9 in which the socket housing and pivot are constructed with biocompatible, sterilizable surgical grade polymer.

14. The endoscope support device of claim 9 in which the socket housing is constructed with biocompatible, sterilizable surgical grade metal and the pivot is constructed with biocompatible, sterilizable surgical grade polymer.

15. The endoscope support device of claim 9 in which the endoscope adapter is constructed with biocompatible, sterilizable surgical grade metal.

16. The endoscope support device of claim 9 in which the endoscope adapter is constructed with biocompatible, sterilizable surgical grade polymer.

17. The endoscope support device of claim 9 in which the endoscope adapter includes a plurality of ribs on the outer wall.

18. The endoscope support device of claim 9 further comprising a skirt positionable at the lower surface of the socket housing extending between the lower surface and the patient.

19. The endoscope support device of claim 18 in which the skirt is constructed with a resilient polymer.

20. The endoscope support device of claim 18 in which the endoscope adapter central bore includes a taper in the central bore at that end of the central bore proximate the lower surface narrowing the inner diameter of the central bore.

* * * * *